United States Patent [19]

Kaye et al.

[11] 4,284,582

[45] Aug. 18, 1981

[54] PROCESS FOR THE PREPARATION OF CYCLOPROPANE DERIVATIVES, INTERMEDIATES IN THE SYNTHESIS OF PYRETHROID INSECTICIDES

[75] Inventors: Albert E. Kaye; Alan C. Tucker, both of Manchester, England

[73] Assignee: Imperial Chemical Industries Limited, London, England

[21] Appl. No.: 177,453

[22] Filed: Aug. 12, 1980

Related U.S. Application Data

[63] Continuation of Ser. No. 28,852, Apr. 10, 1979, abandoned.

[30] Foreign Application Priority Data

Apr. 28, 1978 [GB] United Kingdom ............... 16943/78
Apr. 28, 1978 [GB] United Kingdom ............... 16944/78
Apr. 28, 1978 [GB] United Kingdom ............... 16945/78

[51] Int. Cl.³ .................. C07C 120/00; C07C 121/48
[52] U.S. Cl. ...................................... 260/464; 560/124
[58] Field of Search ........................................ 260/464

[56] References Cited

U.S. PATENT DOCUMENTS

| | | | |
|---|---|---|---|
| 3,239,553 | 3/1966 | Rust et al. ........................ | 260/465.7 |
| 3,354,196 | 11/1967 | Julia ................................ | 260/465.7 X |
| 3,391,205 | 7/1968 | Strain et al. ................... | 260/465.7 X |
| 3,454,657 | 7/1969 | Decker et al. ................ | 260/465.7 X |
| 3,974,199 | 8/1976 | Plonka et al. ................ | 260/464 |
| 4,000,180 | 12/1976 | Punja ............................ | 260/464 |
| 4,083,863 | 4/1978 | Brand ............................ | 260/464 X |
| 4,096,170 | 6/1978 | Van Den Brink ............. | 260/464 X |
| 4,118,412 | 10/1978 | Cleare et al. ................ | 260/464 |
| 4,154,952 | 5/1979 | Schultz ........................ | 260/464 X |
| 4,174,348 | 11/1979 | Kramer et al. ................ | 260/464 |

OTHER PUBLICATIONS

Elliott et al., "Pyrethrum, The Natural Insecticide," (1973), Academic Press, Inc., N.Y., N.Y., pp. 55, 65–66.
Cloke et al., J.A.C.S., 53, (1931), pp. 2791–2797.
Boldt et al., Ber., (100), (1967), pp. 1281–1288.
Kim et al., Tetrahedon, 25, (1969), pp. 3869–3877.
Kim et al., J. Chem. Soc. (C), 1969, pp. 2409–2412.
Hart et al., J. Org. Chem., 28, (1963), pp. 1220–1222.

*Primary Examiner*—Joseph Paul Brust
*Attorney, Agent, or Firm*—Cushman, Darby & Cushman

[57] ABSTRACT

Compounds of formula:

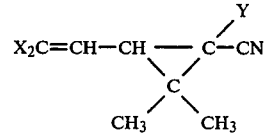

wherein both groups X are chlorine, bromine or trifluoromethyl, or one X is chlorine or bromine and the other is trifluoromethyl, and Y is —CN or —COOR in which R is an alkyl group, are obtained by (A) reacting a compound of the formula:

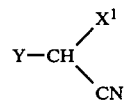

wherein $X^1$ is chlorine or bromine, with a compound of the formula:

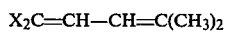

in the presence of metallic copper or at least one copper salt and a base, or (B) reacting a compound of the formula:

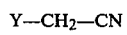

with a compound of the formula:

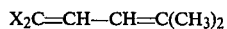

and chlorine or bromine, in the presence of at least one reducible copper salt and a base, or (C) reacting a compound of formula:

X—CH₂—CN with a compound of the formula:

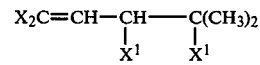

wherein $X^1$ is chlorine or bromine, in the presence of at least one copper salt.

The compounds are intermediates in the synthesis of pyrethroid insecticides.

8 Claims, No Drawings

PROCESS FOR THE PREPARATION OF CYCLOPROPANE DERIVATIVES, INTERMEDIATES IN THE SYNTHESIS OF PYRETHROID INSECTICIDES

CROSS REFERENCE TO RELATED APPLICATIONS

This application is a continuation in part of our earlier application, Ser. No. 28,852, filed Apr. 10, 1979, and now abandoned.

This invention relates to a process for the preparation of cyclopropane derivatives, intermediates in the synthesis of pyrethroid insecticides.

3-(2′,2′-dichlorovinyl)-2,2-dimethylcyclopropane-1-carboxylic acid is an important intermediate in the production of insecticides, including, for example, m-phenoxybenzyl 3-(2′,2′-dichlorovinyl)-2,2-dimethylcyclopropane-1-carboxylate. 3-(2′,2′-dichlorovinyl)-2,2-dimethylcyclopropane-1-carboxylic acid has been prepared, for example, as described by Farkas et al in Collection Czechoslov. Chem. Commun., 1959, 24, pages 2230-2236, by the reaction of ethyl diazoacetate with 1,1-dichloro-4-methyl-1,3-pentadiene followed by hydrolysis of the resultant ethyl ester. This process is not suitable for large scale preparation of the acid because of the difficulties of working with ethyl diazoacetate, which is a substance which can decompose explosively unless the conditions are rigorously controlled, and which is believed to be a potent carcinogen.

3-(2′,2′-dichlorovinyl)-2,2-dimethylcyclopropane-1-carboxylic acid exists in two isomeric forms, according to whether the dichlorovinyl group and the carboxylic acid group are on the same side (cis) or on opposite sides (trans) of the cyclopropane ring. Insecticidal esters, for example, the m-phenoxybenzyl ester, of this carboxylic acid, likewise exist in cis- and trans-isomeric forms. These two forms do not have the same insecticidal potency, the cis-isomer being more active than the trans-isomer. Accordingly it is desirable that a method for the preparation of 3-(2′,2′-dichlorovinyl)-2,2-dimethylcyclopropane-1-carboxylic acid should give the highest possible ratio of cis-isomer to trans-isomer.

The present invention provides a process for the preparation of dihalogenovinyl cyclopropane carboxylic acid derivatives which avoids the use of diazoacetic esters and which also gives a high ratio of cis- to trans-isomer.

According to the present invention there is provided a process for the preparation of a compound of formula:

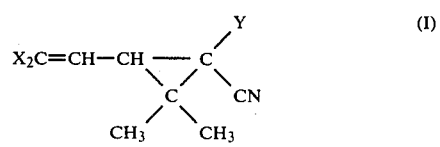

wherein both groups X are chlorine, bromine or trifluoromethyl, or one X is chlorine or bromine and the other is trifluoromethyl, and Y is CN or —COOR in which R is an alkyl radical, characterised in that (A) a compound of the formula:

wherein $X^1$ is chlorine or bromine is reacted with a diene of the formula:

$$X_2C=CH-CH=C(CH_3)_2 \qquad (III)$$

the reaction taking place in the presence of metallic copper or at least one copper salt and a base, or (B) a compound of the formula:

$$Y-CH_2-CN \qquad (IV)$$

is reacted with a diene of the formula:

$$X_2C=CH-CH=C(CH_3)_2 \qquad (III)$$

and chlorine or bromine, in the presence of at least one reducible copper salt and a base, or (C) a compound of formula:

$$Y-CH_2-CN \qquad (IV)$$

is reacted with a compound of the formula:

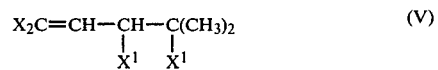

wherein $X^1$ is chlorine or bromine, in the presence of at least one copper salt.

The alkyl radical R preferably contains from 1 to 4 carbon atoms.

With regard to process variant (A):

Examples of the copper salts which may be used are cupric chloride, cupric acetate, cuprous chloride and cuprous cyanide. Mixtures of copper salts may be used. Other useful catalysts are binuclear copper complexes, for example, di-μ-methoxobis(pentane-2,4-dionato)dicopper and di-μ-methoxobis(salicylaldehydato)dicopper.

Examples of the compounds of formula (II) which may be used are methyl bromocyanoacetate and ethyl bromocyanoacetate.

It is preferred to carry out process variant (A) in the presence of at least one alkali or alkaline earth metal salt, for example, a lithium, calcium or magnesium salt, in addition to the copper or copper salt and base. Halides of lithium, calcium or magnesium are especially preferred, although other salts of these metals may also be used. Particularly useful salts of lithium, calcium and magnesium are the chlorides. Optionally a quaternary ammonium salt, for example, a tetra-alkyl ammonium halide such as methyl triethyl ammonium chloride, may be used in the place of or in addition to the lithium, calcium or magnesium salt.

The base which is used is preferably the alkali or alkaline earth metal salt of a weak acid such as carbonic acid or boric acid. Specific examples of such bases are potassium carbonate, borax (sodium tetraborate), calcium carbonate and magnesium carbonate. Other bases which may be used are alkali metal alkoxides such as sodium methoxide and alkaline earth metal oxides such as magnesium oxide. Less desirable are alkali metal salts of carboxylic acids.

The amount of base which is used may be from 0.5 to 2.0, preferably 0.5 to 1.0 moles per mole of the compound of formula (III).

The various metal salts which are used in process variant (A) may be used in the anhydrous or hydrated form. Thus, for example, it is convenient to employ cupric acetate and lithium chloride as their monohydrates. Calcium halides are preferably employed in the anhydrous form when a non-aqueous medium is used.

The copper or copper salt which is used in process variant (A) may be in molar proportion or in even greater amount with respect to the compound of formula (III), but it is preferred to use the copper or copper salt in catalytic amount, for example, from 0.01 to 0.1 mole per mole of the compound of formula (III).

The alkali or alkaline earth metal salt which may also be used in process variant (A) may be employed in an amount from 0 to 5 moles per mole of the diene of formula (III). Preferred amounts are from 2 to 3 moles per mole of the diene of formula (III). Increase in alkaline earth halide concentration tends to increase the cis-cyano to trans-cyano ratio in the compound of formula (I).

Process variant (A) may optionally be carried out in the presence of a solvent or diluent for the reactants, although it may also be conducted in the absence of a solvent or diluent, the reactants themselves being non-viscous liquids although they are not necessarily good solvents for the copper and other salts employed in the process. When a solvent or diluent is used it may be, for example, a polar aprotic solvent or diluent of the type exemplified by dimethylformamide, dimethylsulphoxide or N,N-dimethylacetamide, or a nitrile such as acetonitrile, or an ester such as methyl acetate, ethyl acetate, n-propyl acetate, isopropyl acetate, n-butyl acetate, isobutyl acetate, secondary butyl acetate, tert.butyl acetate, n-pentyl acetate, isopentyl acetate, n-hexyl acetate, cyclohexyl acetate, 2-methoxyethyl acetate or 2-ethoxyethyl acetate, or a halogenated hydrocarbon such as ethylene dichloride or methylene dichloride. Particularly preferred solvents are saturated aliphatic alcohols containing up to six carbon atoms, such as methanol, ethanol, n-propanol, isopropanol, n-butanol, isobutanol, secondary butanol, tert.butanol, n-pentanol, isopentanol or n-hexanol. There may also be used cyclohexanol, 2-methoxyethanol and 2-ethoxyethanol. An especially preferred solvent is ethanol, optionally denatured with small amounts of methanol as in industrial methylated spirit. Water may be used as a diluent for the reaction, particularly when a phase-transfer catalyst such as a quaternary ammonium salt is present. Examples of quaternary ammonium salts particularly useful for this purpose are tetraalkyl ammonium halides such as tetramethyl ammonium chloride, tetrabutyl ammonium chloride, ethyl trimethyl ammonium bromide, methyl triethylammonium chloride and cetyl trimethylammonium bromide, and benzyl trialkylammonium halides such as benzyl trimethylammonium chloride and lauryl benzyldimethylammonium chloride.

Water may also be used as a diluent in admixture with water-miscible solvents such as methanol or ethanol.

It is preferred to employ together an alkali or alkaline earth metal halide and a reaction solvent in which the halide has substantial solubility, in such amounts that the halide forms an almost saturated solution in the solvent. For example, there may be used a solution of calcium chloride in ethanol containing approximately 2 moles/liter, or a solution of calcium chloride in water containing 4.0 to 5.5 moles/liter.

Process variant (A) may be carried out by mixing all of the reactants (and the solvent or diluent when used) together and causing or allowing the reaction to take place. Alternatively, the compound of formula (II) may be added gradually to the remaining reactants as reaction proceeds.

Process variant (A) may be conducted at any temperature within the range 0° C. to the reflux temperature of the reactants and solvent or diluent (when used). However it has been found that the reactions are accelerated by the application of heat and a preferred temperature range for conducting the process is from about 50° C. to about 105° C., although temperatures up to 140° C. may be used.

Process variant (A) may be conducted over a time period of from several minutes to several hours, for example from 30 minutes to 30 hours. A time of about 5 hours is normally sufficient to provide a reasonable yield of product when a temperature in excess of 75° C. is employed.

Certain combinations of copper and other salts are particularly useful in performing process variant (A). These include (a) the use of a molar amount of cupric acetate using acetonitrile, ethanol or dimethylformamide as solvent and a base as hereinbefore defined, (b) the use of a catalytic amount of copper salt in water as solvent together with a phase-transfer catalyst and a base as hereinbefore defined, (c) the use of a catalytic amount of cupric acetate in acetonitrile as solvent and a base as hereinbefore defined, (d) the use of catalytic amounts of cupric acetate, cuprous chloride or cuprous cyanide and bases such as sodium methoxide, calcium carbonate, or magnesium carbonate in methanol as solvent, (e) the use of catalytic amounts of binuclear copper complexes as hereinbefore described and a base such as calcium carbonate or magnesium carbonate, in methanol or ethanol as solvent, and (f) the use of a catalytic amount of copper salt in ethanol as solvent and in the presence of an alkali or alkaline earth metal halide and a base as hereinbefore defined.

With regard to process variant (B):

Examples of the copper salts which may be used are cupric acetate, cupric chloride, cuprous chloride and cuprous cyanide.

Examples of the compounds of formula (IV) which may be used are methyl cyanoacetate, ethyl cyanoacetate, n-propyl cyanoacetate, isopropyl cyanoacetate, n-butyl cyanoacetate and malonitrile.

It is preferred to carry out process variant (B) in the presence of at least one alkali or alkaline earth metal salt, for example, a lithium, calcium or magnesium salt. Halides of lithium, calcium or magnesium are especially preferred, although other salts of these metals may also be used. Particularly useful salts of lithium, calcium and magnesium are the chlorides. Optionally a quaternary ammonium salt, for example, a tetra-alkyl ammonium halide such as methyl triethylammonium chloride or cetyl trimethylammonium bromide or a benzyl trialkylammonium halide such as lauryl benzyl dimethylammonium chloride, may be used in the place of or in addition to the lithium, calcium or magnesium salt.

The base which is used is preferably the alkali or alkaline earth metal salt of a weak acid such as carbonic acid, boric acid or a carboxylic acid (for example acetic acid). Specific examples of such bases are potassium carbonate, borax (sodium tetraborate), potassium acetate, calcium carbonate and magnesium carbonate. Other bases which may be used are alkaline earth metal oxides such as magnesium oxide. The amount of base which is used may be from 1.0 to 4.0, preferably 1.0 to 2.0 moles per mole of the compound of formula (III).

The various metal salts which may be used in process variant (B) may be in the anhydrous or hydrated form. Thus, for example, it is convenient to employ cupric acetate and lithium chloride as their monohydrates. Calcium halides are preferably employed in the anhydrous form when a non-aqueous medium is used.

The copper salt which is used in process variant (B) may be in molar proportion or in even greater amount with respect to the compound of formula (III) but it is preferred to use the copper salt in catalytic amount, for example, about 0.1 mole or even about 0.01 mole per mole of the compound of formula (III).

The amount of chlorine or bromine which is used may be from 0.5 to 2.0 mole per mole of the compound of formula (III), the least amount of halogen being used when using a molar amount of copper salt. Less copper salt requires correspondingly more halogen.

The alkali or alkaline earth metal salt which may also be used in process variant (B) may be employed in an amount from 0 to 6 moles per mole of the compound of formula (III). Preferred amounts are from 2 to 3 moles per mole of the compound of formula (III).

Process variant (B) may optionally be carried out in the presence of a solvent or diluent for the reactants, although it may also be conducted in the absence of a solvent or diluent, the reactants themselves being nonviscous liquids although they are not necessarily good solvents for the copper and other salts employed in the process. When a solvent or diluent is used it should be relatively unreactive (and preferably totally unreactive) towards chlorine or bromine compared with the reactants of formulae (II) and (III). Suitable solvents or diluents are, for example, water and acetonitrile.

The process conditions under which process variant (B) is carried out, i.e. temperature and time of reaction, are the same as for process variant (A).

Certain combinations of copper and other salts are particularly useful in performing process variant (B). These include (a) the use of a molar amount of cupric acetate and 0.5 to 1.0 mole of chlorine or bromine in acetonitrile as solvent, optionally in the presence of lithium chloride, and (b) the use of a catalytic amount of copper salt in water, preferably in the presence of an alkali or alkaline earth metal halide.

Chlorine may be introduced into the reaction mixture by bubbling the gas through the mixture. Bromine may be added dropwise at an appropriate rate.

With regard to process variant (C):

It is preferred that X' is bromine.

Examples of the copper salts which may be used are cupric chloride, cupric acetate, cuprous chloride and cuprous cyanide. Mixtures of copper salts may be used.

Examples of the compounds of formula (IV) which may be used are methyl cyanoacetate, ethyl cyanoacetate, n-propyl cyanoacetate, isopropyl cyanoacetate, and n-butyl cyanoacetate and malononitrile.

Examples of the compounds of formula (V) which may be used are 1,1,3,4-tetrachloro-4-methylpent-1-ene, 1,1-dichloro-3,4-dibromo-4-methylpent-1-ene, 1,1-dibromo-3,4-dichloro-4-methylpent-1-ene and 1,1,3,4-tetrabromo-4-methylpent-1-ene.

It is preferred to carry out process variant (C) in the presence of at least one alkali or alkaline earth metal salt, for example, a lithium, calcium or magnesium salt, in addition to the copper salt. Halides of lithium, calcium and magnesium are especially preferred, although other salts of these metals may also be used. Particularly useful salts of lithium, calcium and magnesium are the chlorides. Optionally a quaternary ammonium salt, for example, a tetra-alkyl ammonium halide such as methyl triethyl ammonium chloride, may be used in the place of or in addition to the lithium, calcium or magnesium salt.

It is further preferred to conduct process variant (C) in the presence of a base which is preferably the alkali or alkaline earth metal salt of a weak acid such as carbonic acid, boric acid or a carboxylic acid (for example, acetic acid). Specific examples of such bases are potassium carbonate, borax (sodium tetraborate), potassium acetate, calcium carbonate and magnesium carbonate. Other bases which may be used are alkali metal alkoxides such as sodium methoxide and alkaline earth metal oxides such as magnesium oxide.

The various metal salts which may be used in process variant (C) may be used in the anhydrous or hydrated form. Thus, for example, it is convenient to employ cupric acetate and lithium chloride as their monohydrates. Calcium halides are preferably employed in the anhydrous form, when a non-aqueous medium is used.

The copper salt which is used in process variant (C) may be in molar proportion or in even greater amount with respect to the compound of formula (V), but it is preferred to use the copper salt in catalytic amount, for example, about 0.1 mole or even about 0.01 mole per mole of the compound of formula (V).

The alkali or alkaline earth metal salt which is employed in process variant (C) may be used in an amount from 0 to 4 moles per mole of the compound of formula (IV). It is preferred to use from 2 to 3 moles per mole of the compound of formula (IV). It is further preferred to employ together an alkali or alkaline earth metal halide and a reaction solvent as hereinafter defined in which the halide has substantial solubility, in such amounts that the halide forms an almost saturated solution in the solvent. For example, there may be used a solution of calcium chloride in ethanol containing approximately 2 moles/liter, or a solution of calcium chloride in water containing 4.0 to 5.5 moles/liter.

The amount of base which is also employed in process variant (C) may be used in an amount from 1 to 2 moles per mole of the compound of formula (V). It is preferred to use approximately 2 moles.

Process variant (C) may optionally be carried out in the presence of a solvent or diluent for the reactants, although it may also be conducted in the absence of a solvent or diluent, the reactants themselves being nonviscous liquids although they are not necessarily good solvents for the copper and other salts employed in the process. When a solvent or diluent is used it may be, for example, any of those solvents, and preferred solvents, which are indicated as suitable for use in process variant (A).

Water may be used as a diluent for the reaction, particularly when a phase transfer catalyst such as a quaternary ammonium salt is present. Examples of quaternary ammonium salts particularly useful as phase transfer catalysts are those indicated as suitable for this purpose in process variant (A).

Water may also be used as a diluent in admixture with water-miscible solvents such as methanol or ethanol.

The process conditions under which process variant (C) is carried out, i.e. temperature and time of reaction, are the same as for process variant (A).

Certain combinations of copper and other salts are particularly useful in performing process variant (C). These include (a) the use of a molar amount of cupric acetate using 1,1-dichloro-3,4-dibromo-4-methylpent-1-ene and ethyl cyanoacetate as reactants, and acetonitrile, ethanol or dimethylformamide as the solvent or diluent, (b) the use of a catalytic amount of a cuprous salt together with sodium methoxide or magnesium carbonate using the same reactants as in (a) and methanol or ethanol as the solvent or diluent; (c) the use of a molar amount of cupric acetate and a molar amount of lithium chloride or, preferably, lithium bromide, using 1,1,3,4-tetrachloro-4-methylpent-1-ene and ethyl cyanoacetate as reactants and acetonitrile as solvent or diluent.

The starting materials of formula (V) which are used in process variant (C) may be obtained by addition of chlorine or bromine to a diene of the formula $X_2C=CH-CH=C(CH_3)_2$, wherein X has the meaning defined above, in a low boiling solvent such as methylene chloride or carbon tetrachloride, followed by evaporation of the solvent. The product may be purified by distillation but this is not essential. Halogenation can also be carried out in the absence of a solvent, but use of a solvent is preferred. The solvent can also be water. A mixture of the compound (V) with the corresponding 1,4-addition product

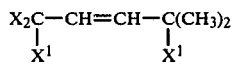

may also be used as starting material.

The direct products of process variants (A), (B) and (C) are compounds of formula (I) as hereinbefore defined. Of particular interest are compounds of formula (I) wherein X is chlorine, for example, methyl or ethyl 1-cyano-3-(2',2'-dichlorovinyl)-2,2-dimethylcyclopropane-1-carboxylate.

The compounds of formula (I) in which Y is not CN obtained by process variants (A), (B) and (C) may readily be converted by hydrolysis and decarboxylation, or preferably by the method described in our German Offenlegungsschrift No. 2751610, into the corresponding carboxylic acids. The latter method can also provide an ester of the carboxylic acid, and enables essentially pure cis- and/or pure trans-isomers to be prepared. In either case the carboxylic acid group in the product takes the place of the original cyano group.

The compounds of formula (I) in which Y is CN, i.e. the dinitrile, may be converted into the corresponding cis-mononitrile by hydrolysis of the trans-nitrile group only to give the 1-cis-nitrile-1-trans-carboxylic acid followed by decarboxylation of the latter to give the 1-cis-nitrile, which may then be further reacted to give the 1-cis-carboxylic acid or carboxylic acid ester, the decarboxylation and subsequent stage being carried out, for example, as described in our German Offenlegungsschrift No. 2751610 already referred to.

The invention is illustrated by the following Examples in which parts and percentages are by weight unless otherwise indicated, and in which the ratio of parts by weight to parts by volume is that of the kilogram to the liter.

EXAMPLE 1

A mixture of 1,1-dichloro-4-methylpenta-1,3-diene (15.1 parts), ethyl bromocyanoacetate (19.2 parts), cupric acetate monohydrate (20 parts), benzyl trimethyl ammonium chloride (4.54 parts) and water (50 parts) is stirred at the reflux temperature of the mixture for 6 hours. After cooling, water (100 parts) and toluene (100 parts by volume) are added, the mixture is stirred at room temperature for 30 minutes and filtered. The filter cake is washed twice with toluene (20 parts by volume). The filtrates are combined and the toluene layer is separated and washed four times with water (50 parts). The toluene layer is evaporated under reduced pressure to yield 18.98 parts of product containing 63.5% of ethyl 1-cyano-3-(2',2'-dichlorovinyl)-2,2-dimethylcyclopropane-1-carboxylate having a cis-cyano:trans-cyano ratio of 68.2:31.8.

EXAMPLES 2-6

The procedure described in Example 1 is repeated except that the phase-transfer catalyst (benzyl trimethyl ammonium chloride) is omitted and the water (50 parts) is replaced by one of the solvents indicated in the table below (100 parts by volume). Reaction is carried out at the reflux temperature of the mixture if this is below 100° C., otherwise at a temperature not exceeding 100° C. After a reaction period of 6 hours the mixture is filtered and the filtrate is evaporated under reduced pressure to remove the solvent. The residue is extracted with a mixture of toluene (100 parts by vol.), water (150 parts) and concentrated hydrochloric acid (100 parts by volume), the extract is filtered and the filter cake is washed with toluene (2×20 parts by volume). The filtrate and washes are combined and the toluene layer is separated and extracted twice with a mixture of water (50 parts) and concentrated hydrochloric acid (50 parts by volume) and then washed four times with water (50 parts). The toluene layer is evaporated under reduced pressure to remove the solvent and yields crude ethyl 1-cyano-3-(2',2'-dichlorovinyl)-2,2-dimethylcyclopropane-1-carboxylate.

In the case of Example 4, the cupric acetate is dried by azeotropic distillation with butyl acetate before addition of the other reactants. On completion of the reaction under the conditions of time and temperature indicated above, the butyl acetate suspension is filtered and the filtrates are extracted with a mixture of water (150 parts) and concentrated hydrochloric acid (100 parts by volume), and then washed with water (4×50 parts). The crude product is isolated by distilling off the butyl acetate under reduced pressure.

Results are as follows:

| Ex. | Solvent | Lithium bromide (parts by weight) | Reaction temp. (°C.) | Strength of product | cis-nitrile trans-nitrile ratio | Yield (%) |
|---|---|---|---|---|---|---|
| 2 | acetonitrile | nil | 76–80 | 63.2 | 71.2:28.8 | 53.6 |
| 3 | acetonitrile | 9.0 | 77–80 | 59.4 | 77.6:22.4 | 51.1 |
| 4 | butyl acetate | nil | 96–100 | 20.0 | 54:46 | 20.7 |

-continued

| Ex. | Solvent | Lithium bromide (parts by weight) | Reaction temp. (°C.) | Strength of product | cis-nitrile trans-nitrile ratio | Yield (%) |
|---|---|---|---|---|---|---|
| 5 | ethanol | nil | 80 | 67.2 | 65.6:34.4 | 52.6 |
| 6 | dimethyl-formamide | nil | 97–100 | 69.5 | 76.1:23.9 | 33.6 |

EXAMPLES 7–12

A mixture of 1,1-dichloro-4-methylpenta-1,3-diene (15.1 parts), copper-containing catalyst in amount indicated in the table below and methanol (32 parts) is heated to reflux and ethyl bromocyanoacetate (19.2 parts) in methanol (14 parts) is then added at a uniform rate during 6 hours, and the acid-base balance ("pH" as indicated by a pH meter) is maintained at a predetermined value by the addition of a 13% solution of sodium methoxide in methanol. On completion of the ethyl bromocyanoacetate addition, heating at reflux temperature is continued for a further 2 hours, maintaining the desired acid-base balance as necessary. The resulting solution is evaporated under reduced pressure to remove the solvent and the product is isolated as described in Examples 2–6 above. The yield, strength and composition of the ethyl 1-cyano-3-(2′,2′-dichlorovinyl)-2,2-dimethylcyclopropane-1-carboxylate obtained are given in the following table together with other reaction details:

| Ex. | Copper catalyst and amount (parts) | Indicated pH | Strength of Product (%) | cis-cyano/trans-cyano ratio | Yield (%) |
|---|---|---|---|---|---|
| 7 | cuprous cyanide (0.9) | 2.0 | 64.4 | 72:28 | 55.7 |
| 8 | cuprous cyanide (0.9) | 2.8 | 69.6 | 72.4:27.6 | 58.4 |
| 9 | cuprous cyanide (0.9) | 7.0 | 44.3 | 61.8:38.2 | 26.4 |
| 10 | copper acetylacetonate (1.3) | 4.0 | 64.9 | 64.2:35.8 | 46.1 |
| 11 | copper stearate (3.2) | 4.0 | 60.7 | 69.3:30.7 | 57.0 |
| 12 | di-μ-methoxo-bis(2,4-pentanedionato)dicopper (0.25) | 4.0 | 65.5 | 65.6:34.4 | 56.1 |

EXAMPLES 13–24

A mixture of 1,1-dichloro-4-methylpenta-1,3-diene (15.1 parts) ethylbromocyanoacetate (19.2 parts), copper-containing catalyst (as indicated in the table below), acid binder (as indicated in the table below) in solvent (as indicated in the table below; 100 parts by volume) is heated to the reflux temperature of the mixture if below 90° C., otherwise at a temperature not exceeding 90° C., and held at the reaction temperature for 6 hours. After removal of the solvent by distillation under reduced pressure the residue is extracted with a mixture of toluene (100 parts by volume), water (150 parts) and concentrated hydrochloric acid (100 parts by volume). The extract is filtered, the toluene layer is separated, washed with water (4×50 parts) and the crude ethyl-1-cyano-3-(2′,2′-dichlorovinyl)-2,2-dimethylcyclopropane-1-carboxylate is isolated by distilling off the toluene under reduced pressure. The yield, strength and composition of the product obtained is given in the table below together with other reaction details.

| Ex | Acid binder and amount (parts) | Solvent | Copper catalyst and amount (parts) | Reaction temperature (°C.) | Strength of product (%) | cis-cyano/trans-cyano ratio | Yield |
|---|---|---|---|---|---|---|---|
| 13 | ferric acetate (22.2) | acetonitrile | cupric chloride (1.34) | 83–84 | 52.9 | 73.9:26.1 | 42.0 |
| 14 | magnesium oxide (4) | methanol | cuprous cyanide (0.9) | 65–66 | 42.6 | 65.2:34.8 | 29.8 |
| 15 | calcium carbonate (10) | ethanol | di-μ-methoxo-bis salicylaldehydato) dicopper (0.86) | 77–79 | 58.3 | 76.8:23.2 | 50.3 |
| 16 | calcium carbonate (10) | n-propanol | cupric chloride (1.34) | 82–89 | 60.8 | 74.1:25.9 | 60.8 |
| 17 | calcium carbonate (10) | n-butanol | cupric chloride (1.34) | 82–90 | 53.8 | 73.4:26.6 | 53.8 |
| 18 | calcium carbonate (10) | dimethyl-formamide | cupric chloride (1.34) | 82–85 | 74.7 | 81:19 | 30.0 |
| 19 | magnesium carbonate (8.44) | ethanol | cupric chloride (1.34) | 75–79 | 72.4 | 84.5:15.5 | 61.1 |
| 20 | calcium carbonate (6) | " | cuprous chloride (0.1) | 77–78 | 65.3 | 84.5:15.5 | 54.0 |
| 21 | calcium carbonate (20) | " | cuprous chloride (0.1) | 80 | 73.0 | 86.9:13.1 | 61.6 |
| 22 | calcium carbonate (10) | " | cupric oxide (0.8) | 77–78 | 65.5 | 85:15 | 56.5 |
| 23 | calcium carbonate (10) | " | copper bronze (0.646) | 77–79 | 65.0 | 86:14 | 29.9 |
| 24 | calcium carbonate (10) (+ calcium chloride 22.2) | " | cuprous chloride (0.1) | 82–85 | 76.8 | 86.8:13.2 | 68.2 |

EXAMPLE 25

A mixture of 1,1-dichloro-4-methylpenta-1,3-diene (30.2 parts) and ethyl bromocyanoacetate (19.2 parts) is heated in ethanol (100 parts by volume) at 77°–80° C.

for 6 hours in the presence of cupric chloride (1.34 parts) and calcium carbonate (10 parts). The crude ethyl 1-cyano-3-(2',2'-dichlorovinyl)-2,2-dimethylcyclopropane-1-carboxylate is isolated as described in Examples 13–24. The product has a strength of 61.0% and a cis-cyano/trans-cyano ratio of 85.2:14.8. The yield is 56.5%.

EXAMPLE 26

A mixture of 1,1-dichloro-4-methylpenta-1 3-diene (15.1 parts), ethyl bromocyanoacetate (19.2 parts), methyl triethyl ammonium chloride (3.0 parts) and copper stearate (3.16 parts) in water (50 parts) is heated to 60° C. and held at 60°–65° C. for 6 hours. 2 N-Aqueous sodium carbonate solution is added throughout the heating period to maintain the pH at 3.0–3.3 (14.6 parts by volume required). The mixture is cooled, water (100 parts), toluene (100 parts by volume) and concentrated hydrochloric acid (100 parts by volume) are added and the mixture is stirred at room temperature for 30 minutes, after which the toluene layer is separated and washed with water (5×50 parts). The crude ethyl 1-cyano-3-(2',2'-dichlorovinyl)-2,2-dimethylcyclopropane-1-carbonxylate is isolated by removal of the toluene under reduced pressure. The product has a strength of 27.2% and a cis-cyano-trans-cyano ratio of 62.5:37.5. The yield is 30.2%.

EXAMPLES 27–33

A mixture of 1,1-dichloro-4-methylpenta-1,3-diene (30.2 parts), ethyl bromocyanoacetate (38.4 parts), calcium carbonate (20 parts), copper catalyst, phase transfer catalyst and calcium or sodium chloride (each as indicated in the table below) and water (100 parts) is heated at 80° C. and held at 80° C. for 6 hours. The reaction mixture is cooled and stirred with water (100 parts), butyl acetate (100 parts by volume) and concentrated hydrochloric acid (100 parts by volume). The mixture is filtered and the residue is washed with butyl acetate (2×20 parts by volume). The filtrate and washes are combined and the butyl acetate layer is separated and washed with water (4×50 parts). The crude ethyl-1-cyano-3-(2',2'-dichlorovinyl)-2,2-dimethylcyclopropane-1-carboxylate is isolated by removal of the butyl acetate under reduced pressure.

Details are given in the following table:

cium carbonate (20 parts), cuprous chloride (0.2 part) and calcium chloride (22.2 parts) in ethanol (100 parts by volume) is heated to reflux temperature and held at 78°–84° C. for 6 hours. The ethanol is distilled off under reduced pressure and the residue is stirred with a mixture of toluene (100 parts by volume), water (150 parts) and concentrated hydrochloric acid (100 parts by volume). The mixture is filtered from extraneous matter, the residue is washed with toluene and the filtrate and washings are combined. The toluene layer is separated and washed with water. The crude ethyl 1-cyano-3-(2',2'-dichlorovinyl)-2,2-dimethylcyclopropane-1-carboxylate is isolated by removal of the toluene under reduced pressure. The product has a strength of 74.6% and a cis-cyano/trans-cyano ratio of 86.1:13.9. The yield is 68.7%.

EXAMPLE 35

The procedure described in Example 34 is repeated except that the ethyl bromocyanoacetate (38.4 parts) is replaced by ethyl chlorocyanoacetate (29.52 parts). Ethyl 1-cyano-3-(2',2'-dichlorovinyl)-2,2-dimethylcyclopropane-1-carboxylate having a strength of 70.5% and a cis-cyano/trans-cyano ratio of 73.5:26.5 is obtained in 57.9% yield.

EXAMPLE 36

The procedure described in Example 35 is repeated with the addition of potassium bromide (2.38 parts). Ethyl 1-cyano-3-(2',2'-dichlorovinyl)-2,2-dimethylcyclopropane-1-carboxylate having a strength of 72.9% and a cis-cyano/trans-cyano ratio of 70.7:29.3 is obtained in 60.2% yield.

EXAMPLE 37

The procedure described in Example 28 is repeated except that the ethyl bromocyanoacetate (38.4 parts) is replaced by ethyl chlorocyanoacetate (29.52 parts). Ethyl 1-cyano-3-(2',2'-dichlorovinyl)-2,2-dimethylcyclopropane-1-carboxylate having a strength of 68.8% and a cis-cyano/trans-cyano ratio of 69.9:30.1 is obtained in 61.9% yield.

EXAMPLE 38

A mixture of 1,1-dibromo-4-methylpenta-1,3-diene (24 parts), ethyl bromocyanoacetate (38.4 parts), cu-

| Ex | Phase transfer catalyst and amount (parts) | Copper catalyst and amount (parts) | Calcium or sodium chloride and amount (parts) | Strength of product (%) | cis-cyano/ trans-cyano ratio | Yield (%) |
|---|---|---|---|---|---|---|
| 27 | cetyl trimethyl ammonium bromide (1.8) | cupric chloride (2.68) | nil | 57.8 | 63.8:36.2 | 41.7 |
| 28 | cetyl trimethyl (1.8) ammonium bromide | cupric chloride (2.68) | CaCl$_2$ (44.0) | 75.4 | 70.5:29.5 | 68.6 |
| 29 | cetyl trimethyl (1.8) ammonium bromide | cupric chloride (2.68) | NaCl (46.8) | 75.5 | 68.6:31.4 | 66.4 |
| 30 | cetyl trimethyl (1.8) ammonium bromide | cupric chloride (2.68) | CaCl$_2$ (60.0) | 75.6 | 70.4:29.6 | 72.0 |
| 31 | cetyl trimethyl (1.8) ammonium bromide | cupric chloride (2.68) | CaCl$_2$ (88.0) | 71.9 | 70:30 | 67.8 |
| 32 | cetyl trimethyl (1.8) ammonium bromide | cuprous chloride (0.2) | CaCl$_2$ (44.0) | 60.4 | 65.7:34.3 | 50.8 |
| 33 | methyl triethyl (6.0) ammonium chloride | cupric chloride (2.68) | CaCl$_2$ (44.0) | 48.1 | 66.1:33.9 | 46.7 |

EXAMPLE 34

A mixture of 1,1-dichloro-4-methylpenta-1,3-diene (30.2 parts), ethyl bromocyanoacetate (38.4 parts), calprous chloride (1.0 part) and calcium carbonate (20.0 parts) in ethanol (100 parts by volume) is heated to reflux and held at 77°–81° C. for 9.5 hours. The ethanol is distilled off under reduced pressure and the residue stirred with a mixture of toluene (100 parts by volume), water (150 parts) and concentrated hydrochloric acid (100 parts by volume), at room temperature for 1.5 hours. The mixture is filtered from extraneous matter, the residue is washed with toluene and the combined filtrates and washes are allowed to separate. The toluene layer is washed with water (4×50 parts) and then distilled under reduced pressure to remove the solvent and yield product (42.0 parts) which is shown to be essentially pure ethyl 1-cyano-3-(2′,2′-dibromovinyl)-2,2-dimethylcyclopropane-1-carboxylate, as characterised by GLC and NMR.

EXAMPLE 39

A mixture of 1,1-dichloro-4-methylpenta-1,3-diene (12.0 parts), bromomalononitrile (11.5 parts), cuprous chloride (0.8 parts), calcium chloride (17.6 parts) and calcium carbonate (15.9 parts) in ethanol (79.4 parts by volume) is heated to reflux and held at 78°–80° C. for 6 hours. The ethanol is distilled off under reduced pressure and the residue is extracted with a mixture of toluene (100 parts by volume), water (150 parts) and concentrated hydrochloric acid (100 parts by volume).

The resultant mixture is filtered and the residue is well washed with toluene. The combined toluene filtrates and washes are separated, washed with water (4×50 parts) and distilled under reduced pressure to yield 3-(2′,2′-dichlorovinyl)-1,1-dicyano-2,2-dimethylcyclopropane of 90.4% strength in 79.0% yield.

EXAMPLE 40

A mixture of 2-chloro-5-methyl-1,1,1-trifluorohexa-2,4-diene (18.45 parts), ethyl bromocyanoacetate (28.8 parts), cuprous chloride (1.0 part) and calcium carbonate (15 parts) in ethanol (100 parts by volume) is heated to reflux and held at 78°–79° C. for 11.5 hours. The ethanol is distilled off under reduced pressure and the residue is extracted with a mixture of toluene (100 parts by volume), water (150 parts) and concentrated hydrochloric acid (150 parts by volume). After filtering from extraneous matter the filtrates are allowed to separate and the toluene layer is washed with water (4×50 parts). The toluene is removed by distillation under reduced pressure to yield product (24.52 parts) identified by GLC, Mass Spectrum and NMR as ethyl 3-(2-chloro-3,3,3-trifluoropropenyl)-1-cyano-2,2-dimethylcyclopropane-1-carboxylate.

EXAMPLES 41–48

A mixture of ethyl cyanoacetate (12.44 parts), 1,1-dichloro-4-methylpenta-1,3-diene (15.1 parts), copper acetate monohydrate and in some cases lithium or potassium halide as indicated in the table below, is stirred in acetonitrile or acetic acid at an elevated temperature. Bromine is added at a uniform rate and heating is continued for a further period. The reaction mixture is cooled to room temperature and filtered. The insoluble material is washed with solvent and the combined filtrate and washings are distilled under reduced pressure to remove the solvent. The residue is extracted with a mixture of toluene (100 parts by volume), water (150 parts) and concentrated hydrochloric acid (100 parts by volume). The extracts are filtered to remove extraneous matter and the toluene layer is separated, washed twice with a mixture of concentrated hydrochloric acid (50 parts by volume) and water (50 parts), then with water (4×50 parts) and finally distilled under reduced pressure to remove the toluene, the residue being crude ethyl 1-cyano-3-(2′,2′-dichlorovinyl)-2,2-dimethylcyclopropane-1-carboxylate. Details of the reaction conditions are given in the following table together with the yield, strength and composition of the product.

| Ex | Copper acetate (parts) | Metal halide and amount (parts) | Solvent amount and (parts by volume) | Bromine (parts) | Bromine addition Time (hours) | Bromine addition Temp. (°C.) | Further reaction Time (hours) | Further reaction Temp. (0° C.) | Strength (%) | cis-cyano/ trans-cyano ratio | Yield (%) |
|---|---|---|---|---|---|---|---|---|---|---|---|
| 41 | 40 | — | CH3CN 100 | 16 | 2 | 77–82 | 4 | 80–82 | 54.0 | 69.8:30.2 | 51.7 |
| 42 | 40 | — | CH3CN 100 | 8 | 2 | 78–82 | 4 | 78–82 | 61.1 | 68.1:31.9 | 54.0 |
| 43 | 20 | LiCl.H2O (6.26) | CH3CN 100 | 8 | 2 | 75–80 | 4 | 75–80 | 75.2 | 78.1:21.9 | 55.3 |
| 44 | 40 | KCl (7.74) | CH3CN 100 | 8 | 2 | 77–82 | 4 | 82–83 | 63.5 | 69.6:30.4 | 53.5 |
| 45 | 40 | LiBr (9.04) | CH3CN 100 | 8 | 2.5 | 81–84 | 4 | 83–84 | 83.0 | 73:27 | 59.1 |
| 46 | 20 | — | CH3CN 100 | 16 | 4 | 78∝83 | 4 | 79–84 | 43.8 | 72.4:27.6 | 40.4 |
| 47 | 20 | LiBr (9.04) | CH3CN 100 | 8 | 4.33 | 79–84 | 6 | 82–85 | 66.6 | 88.3:11.7 | 38.7 |
| 48 | 40 | — | Acetic acid 100 | 16 | 4.25 | 80–88 | 3.75 | 84–91 | 28.5 | 67:33 | 17.7 |

EXAMPLE 49

A mixture of ethyl cyanoacetate (12.44 parts), 1,1-dichloro-4-methylpenta-1,3-diene (15.1 parts), copper acetate monohydrate (40 parts), lithium chloride monohydrate (6.26 parts) in acetonitrile (200 parts by volume) is heated to reflux temperature. Sodium hypochlorite solution (68 parts by volume, equivalent to 3.54 parts of chlorine) is added at a uniform rate over 1.5 hours, maintaining the reaction temperature at 78°–81° C. Reflux temperature (78°–79° C.) is maintained for a further 4.5 hours. After cooling the mixture, the upper olive green acetonitrile solution is decanted from the light blue suspended salts and the acetonitrile is removed by distillation under reduced pressure. The residue (22.62 parts) is stirred for 1.5 hours at room temperature with toluene (100 parts by volume), water (200 parts) and sodium carbonate (25.8 parts), and the mixture is filtered to remove black, tarry insoluble material (1.34 parts). The toluene layer is separated and washed with water (4×50 parts). The toluene is distilled off under reduced pressure to yield crude ethyl 1-cyano-3-(2′,2′-dichlorovinyl)-2,2-dimethylcyclopropane-1-carbonxylate (15.9 parts) having a strength of 44.9% and a cis-cyano/trans-cyano ratio of 71:29.

EXAMPLES 50–53

A mixture of ethyl cyanoacetate (12.44 parts), 1,1-dichloro-4-methylpenta-1,3diene (15.1 parts), lithium chloride monohydrate (6.26 parts), cupric acetate monohydrate, and in one case potassium acetate, as indicated in the table below, in acetonitrile (100 parts by volume), is heated and chlorine is added at a uniform rate, heating being continued for a further period. After cooling the reaction mixture the acetonitrile is removed by distillation under reduced pressure and the ethyl 1-cyano-3-(2',2'-dichlorovinyl)-2,2-dimethylcyclopropane-1-carboxylate is isolated as described for Examples 41 to 48. The yield, strength and composition of the product, together with other preparative details, are given in the table below.

EXAMPLE 62

A mixture of ethyl cyanoacetate (12.44 parts), 1,1-dichloro-3,4-dibromo-4-methylpent-1-ene (31.1 parts) cupric acetate monohydrate (40 parts) and lithium chloride monohydrate (6.2 parts) in acetonitrile (100 parts) is stirred at 76°–80° C. for 6 hours. The reaction mixture is cooled to room temperature, filtered, and the filter-cake

| Ex | Copper acetate (parts) | Potassium acetate (parts) | Chlorine (parts) | Chlorine addition Time (hours) | Chlorine addition Temp. (°C.) | Further reaction Time (hours) | Further reaction Temp. (°C.) | Strength (%) | cis-cyano/ trans-cyano ratio | Yield (%) |
|---|---|---|---|---|---|---|---|---|---|---|
| 50 | 20 | — | 7.4 | 1.75 | 30–83 | 4.5 | 82–84 | 45.9 | 71.5:28.5 | 37.9 |
| 51 | 20 | — | 12.0 | 0.58 | 82–85 | 5.42 | 85–87 | 50.0 | 68:32 | 40.8 |
| 52 | 20 | — | 3.6 | 2.25 | 80–85 | 3.75 | 85–86 | 69.5 | 71.4:28.6 | 55.9 |
| 53 | 2 | 9.8 | 4.8 | 1.50 | 82–83 | 4.0 | 83–85 | 33.4 | 72.5:27.5 | 20.8 |

EXAMPLES 54–61

A mixture of ethyl cyanoacetate (24.88 parts), 1,1-dichloro-4-methylpenta-1,3-diene (30.2 parts) cupric chloride (2.68 parts), calcium carbonate (40 parts), calcium chloride and potassium bromide as indicated in the table below, is heated in water in the presence of a phase transfer catalyst (either cetyl trimethyl ammonium bromide (CTMAB) or methyl triethyl ammonium chloride (MTEAC)]]. Sodium hypochlorite solution, bromine or chlorine are then added at a uniform rate to the mixture at an elevated temperature. Heating is continued for a further period. After cooling the reaction mixture, the suspension is diluted with butyl acetate (100 parts by volume). Concentrated hydrochloric acid (50 parts by volume) diluted with water (100 parts) is slowly added, the mixture is stirred for about 30 minutes and then filtered to remove extraneous matter. The butyl acetate layer is separated and washed with water (4×50 parts). The butyl acetate is removed by distillation under reduced pressure to yield crude ethyl 1-cyano-3-(2',2'-dichlorovinyl)-2,2-dimethylcyclopropane -1-carboxylate. Details of the reaction conditions are given in the table below, together with the yield, strength and composition of the product.

washed with acetonitrile. The filtrates and washes are combined and distilled under reduced pressure to remove the solvent. The residue is extracted with a mixture of toluene (100 parts by volume), water (150 parts) and concentrated hydrochloric acid (100 parts by volume). The toluene layer is washed with concentrated hydrochloric acid (50 parts by volume) diluted with water (50 parts) and then four times with water (50 parts). The crude ethyl 1-cyano-3-(2',2'-dichlorovinyl)-2,2-dimethylcyclopropane-1-carboxylate is isolated by distilling off the toluene under reduced pressure. The product, strength 60.8% and cis-cyano/trans-cyano ratio 73.5:26.5, is obtained in 38.6% yield.

EXAMPLES 63–71

A mixture of ethyl cyanoacetate (12.44 parts), 1,1-dichloro-3,4-dibromo-4-methylpent-1-ene and in some cases, 1,1-dichloro-4-methylpenta-1,3-diene, copper salt and in some cases lithium halide is heated in a water-miscible solvent. After completion of reaction the resultant ethyl 1-cyano-3-(2',2'-dichlorovinyl)-2,2-dimethylcyclopropane-1-carboxylate is isolated as described in Example 62.

In Example 71 the reaction solvent is anhydrous acetic acid. This is achieved by the use of glacial acetic acid (78 parts) and acetic anhydride (22 parts, equiva-

| Ex | Metal halide and amount (parts) | Water (parts) | Phase transfer catalyst and amount (parts) | Halide (parts) | Halide addition Time (hours) | Halide addition Temp. (°C.) | Further reaction Time (hours) | Further reaction Temp. (°C.) | Strength (%) | cis-cyano/ trans-cyano ratio | Yield (%) |
|---|---|---|---|---|---|---|---|---|---|---|---|
| 54 | CaCl₂ (22.0) | 50 | CTMAB (1.8) | NaOCl soln = 29.8 parts Cl₂ | 2.25 | 80–86 | 6 | 80–89 | 26.8 | 67.9:32.1 | 24.5 |
| 55 | (CaCL₂ (22.0) (KBr (4.76) | 50 | CTMAB (1.8) | NAOCl soln =29.8 parts Cl₂ | 3 | 75–85 | 6 | 82–84 | 40.5 | 67.2:32.8 | 43.4 |
| 56 | CaCl₂ (66) | 100 | MTEAC (6.06) | Br₂ (32) | 0.58 | 48–60 | 0.42 / 0.50 / 5.5 | 58–68 / 52–79 / 79–82 | 77.7 | 67.8:32.2 | 70.1 |
| 57 | CaCl₂ (162) | 100 | MTEAC (6.06) | Br₂ (32) | 0.58 | 64–69 | 0.42 / 0.50 / 6.0 | 60–64 / 64–79 / 79–82 | 66.6 | 66:34 | 70.3 |
| 58 | CaCl₂ (132) | 100 | MTEAC (6.06) | Br₂ (32) | 0.25 | 27–28 | 0.25 / 1.166 / 6.0 | 27–28 / 25–82 / 82–83 | 63.2 | 65.5:34.5 | 65.8 |
| 59 | nil | 100 | MTEAC (6.06) | Br₂ (32) | 0.75 | 46–52 | 1.33 / 6.0 | 52–80 / 80–84 | 37.5 | 63.5:36.5 | 33.0 |
| 60 | CaCl₂ (66) | 100 | MTEAC (6.06) | Cl₂ (14.2) | 4.75 | 72–8 | 6.0 | 77–82 | 24.9 | 67.5:32.5 | 17.9 |
| 61 | CaCl₂ (66) KBr (2.38) | 100 | MTEAC (6.06) | Cl₂ (14.2) | 4.166 | 68–72 | 7.0 | 76–82 | 27.3 | 68.5:31.5 | 23.6 | lent to the water of hydration contained in the copper and lithium salts).

Details of the reaction are given in the following table which also gives the yield, strength and composition of the product.

EXAMPLES 74–76

A mixture of ethyl cyanoacetate (12.44 parts), 1,1,3,4-tetrachloro-4-methylpent-1-ene (11.1 parts), 1,1-dichloro-4-methylpenta-1,3-diene (7.55 parts), cupric

| Ex | Copper salt and amount (parts) | Lithium salt and amount (parts) | Ethyl cyano-acetate (parts) | Diene (parts) | 3:4 dibromo parts | Solvent (parts by volume) | Reaction conditions Time (hours) | Reaction conditions Temp. (°C.) | Strength (%) | cis-cyano trans-cyano ratio | Yield (%) |
|----|---|---|---|---|---|---|---|---|---|---|---|
| 63 | cupric acetate (40) H₂O | LiCl·H₂O (6.26) | 12.44 | 7.55 | 15.5 | CH₃CN (100) | 5 | 81–83 | 76.8 | 69.1:30.9 | 53.2 |
| 64 | cupric acetate (40) H₂O | — | 12.44 | — | 31.1 | CH₃CN (100) | 5 | 78–83 | 64.3 | 69.8:30.2 | 52.7 |
| 65 | Basic cupric carbonate (47.8) | LiCl·H₂O (6.26) | 12.44 | — | 31.1 | CH₃CN (100) | 6 | 76–80 | 72.6 | 72.7:27.3 | 41.7 |
| 66 | cupric acetate (40) H₂O | LiBr (9.04) | 12.44 | — | 31.1 | CH₃CN (100) | 5 | 81–84 | 69.4 | 75.8:24.2 | 52.2 |
| 67 | cupric acetate (20) H₂O | — | 12.44 | — | 31.1 | (CH₃)₃COH (100) | 6 | 80–83 | 20.9 | 61.2:38.8 | 21.2 |
| 68 | cupric acetate (10) H₂O | — | 6.22 | — | 15.56 | EtOH (100) | 69½ | 19–23 | 4.8 | 49.3:50.7 | 5.2 |
| 69 | cupric acetate (20) H₂O | — | 12.44 | — | 31.1 | EtOH (100) | 6 | 73–80 | 40.1 | 67.6:32.4 | 36.8 |
| 70 | cupric acetate (20) H₂O | — | 12.44 | — | 31.1 | DMF (100) | 6 | 85–90 | 63.9 | 80.1:19.9 | 36.7 |
| 71 | cupric acetate (20) H₂O | LiCl·H₂O (6.26) | 12.44 | 7.55 | 15.56 | HOAc (100) | 6 | 89–101 | 65.7 | 83.0:17.0 | 30.8 |

EtOH = ethanol; DMF = dimethylformamide; HOAC = acetic acid

EXAMPLE 72

A mixture of cupric acetate monohydrate (40 parts) and lithium chloride monohydrate (6.26 parts) in n-butyl acetate (100 parts) is heated under reflux, removing water azeotropically until the mixture is dry. Ethyl cyanoacetate (12.44 parts) and 1,1-dichloro-3,4-dibromo-4-methylpent-1-ene (31.1 parts) are added and the mixture is stirred at 123°–125° C. for 5 hours. The reaction mixture is cooled to room temperature, filtered and the filter-cake washed with n-butyl acetate. The filtrate and washes are combined and stirred with water (200 parts) and sodium carbonate (25.8 parts). The precipitated copper carbonate is removed by filtration and washed twice with n-butyl acetate (20 parts by volume). The filtrates and washes are separated, the butyl acetate layer washed four times with water (50 parts) and evaporated under reduced pressure to give ethyl 1-cyano-3-(2',2'-dichlorovinyl)-2,2-dimethylcyclopropane-1-carboxylate strength 54.6% and cis-cyano:trans-cyano ratio 78.2:21.8, in 19.6% yield.

EXAMPLE 73

A mixture of ethyl cyanoacetate (12.44 parts), 1,1-dichloro-3,4-dibromo-4-methylpent-1-ene (31.1 parts), cupric acetate monohydrate (20 parts), benzyltriethylammonium chloride (4.54 parts) and water (100 parts) is stirred at 95°–100° C. for 6 hours. The mixture is cooled and diluted with water (100 parts and toluene (100 parts by volume), and filtered to remove insoluble material. The filter-cake is washed twice with toluene (20 parts by volume) and twice with water (50 parts). The filtrates and washes are separated and the toluene layer is washed with concentrated hydrochloric acid (50 parts by volume) diluted with water (50 parts) and then four times with water (50 parts). The toluene is removed by evaporation under reduced pressure to give ethyl 1-cyano-3-(2',2'-dichlorovinyl)-2,2-dimethylcyclopropane-1-carboxylate, strength 53.3% and cis-cyano:trans-cyano ratio 69.2:30.8 in 31.2% yield.

acetate H₂O (2.0 parts) and in two cases lithium halide, in acetonitrile (100 parts by volume) is heated to reflux and held at 75°–80° C. for 6 hours. After cooling to room temperature the suspension is filtered and the residue is washed twice with acetonitrile (20 parts by volume). The combined filtrate and washes are distilled under reduced pressure to remove acetonitrile and the residue is extracted with a mixture of toluene (100 parts by volume), water (150 parts by volume) and concentrated hydrochloric acid (100 parts by volume). After filtering from extraneous matter the filtrates are separated and the toluene layer is washed twice with hydrochloric acid (50 parts by volume) diluted with water (50 parts) and finally four times with water (50 parts). The toluene is removed by distillation under reduced pressure to yield crude ethyl 1-cyano-3-(2',2'-dichlorovinyl)-2,2-dimethylcyclopropane-1-carboxylate. Details are given in the following table:

| Ex. | Lithium halide and amount (parts) | Strength (%) | cis-cyano: trans-cyano ratio | Yield (%) |
|-----|---|---|---|---|
| 74 | — | 27.2 | 70.2:29.8 | 20.1 |
| 75 | LiCl·H₂O (6.26) | 33.3 | 75.7:24.3 | 20.4 |
| 76 | LiBr (9.02) | 54.9 | 74.1:25.9 | 37.9 |

EXAMPLE 77

1,1-Dichloro-3,4-dibromo-4-methylpent-1-ene (31.1 parts) cuprous chloride (1 part) and methanol (46 parts by volume) are heated to reflux. Ethylcyanoacetate (12.44 parts) in methanol (36 parts) is added at a uniform rate over 4 hours. 15 Minutes after the start of this addition sodium methylate (10.8 parts) in methanol (55 parts by volume) is added at a uniform rate over 5½ hours. The reaction is maintained at reflux for a further 2 hours. After cooling to room temperature the brown solution is filtered from extraneous matter and the filtrate is distilled under reduced pressure to remove methanol. The residue is extracted with a mixture of toluene (100 parts by volume), water (150 parts by volume) and hydrochloric acid (100 parts by volume). The extract is filtered from insoluble matter and the filtrate is separated. The toluene layer is then washed four times with water (50 parts) and the crude ethyl 1-cyano-3-(2',2'-dichlorovinyl)-2,2-dimethylcyclopropane-1-carboxylate is isolated by distilling off the toluene under reduced pressure. A yield of 35.8% of product, strength 63.7% and cis-cyano:trans-cyano ratio 69.9:30.1, is obtained.

EXAMPLES 78-90

A mixture of 1:1-dichloro-3,4-dibromo-4-methylpent-1-ene (31.1 parts), ethylcyanoacetate (12.44 parts), copper salt as catalyst and metal carbonate is heated for 6 hours in a solvent (100 parts by volume). The crude ethyl 1-cyano-3-(2',2'-dichlorovinyl)-2,2-dimethylcyclopropane-1-carboxylate is isolated in a similar manner to Example 77. The copper salt, metal carbonate and solvent are specified in the following table which also gives the yield, strength and composition of the derived ethyl 1-cyano-3-(2',2'-dichlorovinyl)-2,2-dimethylcyclopropane-1-carboxylate.

heated in ethanol (100 parts by volume) at reflux in the presence of calcium chloride (22.2 parts) and copper salt as catalyst. The crude ethyl 1-cyano-3-(2',2'-dichlorovinyl)-2,2-dimethylcyclopropane-1-carboxylate is isolated as described in Example 77. Details are given in the following table:

| Ex. | Copper catalyst and amount (parts) | CaCO₃ (parts) | Ethyl cyano acetate (parts) | 3:4 Dibromo compound and amount (parts) | Reaction Time hrs. | Reaction Temp (°C.) | Strength (%) | Cis-cyano: trans-cyano ratio | Yield (%) |
|---|---|---|---|---|---|---|---|---|---|
| 91 | CuCl₂ (1.34) | 20.0 | 12.44 | 31.1 | 6 | 78-83 | 73.4 | 88:12 | 63.7 |
| 92 | Cu₂Cl₂ (0.2) | 20.0 | 12.44 | 31.1 | 18 | 82-85 | 71.3 | 88.5:11.5 | 61.1 |
| 93 | Cu₂Cl₂ (0.2) | 40.0 | 24.88 | 62.2 | 4.75 | 80-88 | 66.8 | 87.4:12.6 | 55.0 |

EXAMPLES 94-106

A mixture of ethyl cyanoacetate (24.88 parts), 1,1-dichloro-3,4-dibromo-4-methylpent-1-ene (62.2 parts), calcium or magnesium carbonate and metal chloride is heated in water (100 parts) in the presence of a phase transfer catalyst (either cetyl trimethyl ammonium bromide (CTMAB) or methyl triethyl ammonium chloride (MTEAC)]] and a copper salt as catalyst. The reaction mass is cooled to room temperature, n-butyl acetate (100 parts by volume) water (100 parts) and hydrochloric acid (100 parts by volume) are added and the mixture is stirred for 30 minutes, filtered from extraneous matter and the filtrates separated. The butyl acetate layer is washed with water (4×100 parts) and evaporated under reduced pressure to remove the butyl acetate and yield the crude ethyl 1-cyano-3-(2',2'-dichlorovinyl)-2,2-dimethyl-cyclopropane-1-carboxylate. The yield, strength and composition of the product is given in the following table, together with other details.

| Ex. | Copper catalyst and amount (parts) | Acid binder and amount (parts) | Solvent and amount (parts by volume) | Reaction Temp (°C.) | Strength (%) | cis-cyano trans-cyano ratio | Yield (%) |
|---|---|---|---|---|---|---|---|
| 78 | CuCN (0.9) | MgCO₃ (10.12) | methanol (100) | 63-65 | 48.2 | 64.3:35.7 | 35.4 |
| 79 | CuCl₂ (1.34) | Na₂CO₃ (10.6) | ethanol (100) | 79 | 55.0 | 69.4:30.6 | 35.1 |
| 80 | CuCl₂ (1.34) | Na₂CO₃ (21.2) | ethanol (100) | 78-80 | 57.5 | 66.7:33.3 | 21.2 |
| 81 | CuCl₂ (1.34) | MgCO₃ (8.44) | ethanol (100) | 79-81 | 52.7 | 78:22 | 36.9 |
| 82 | CuCl₂ (1.34) | MgCO₃ (16.88) | ethanol (100) | 77-82 | 60.6 | 85.5:14.5 | 46.8 |
| 83 | CuCl₂ (1.34) | CaCO₃ (10) | ethanol (100) | 79-80 | 47.8 | 79.7:20.3 | 29.6 |
| 84 | CuCl₂ (1.34) | CaCO₃ (20) | ethanol (100) | 80-81 | 65.8 | 85.9:14.1 | 51.7 |
| 85 | CuCl₂ (1.34) | MgCO₃ (16.88) | methanol (100) | 67-68 | 66.8 | 85:15 | 26.9 |
| 86 | CuCl₂ (1.34) | CaCO₃ (20) | methanol (100) | 64-68 | 69.15 | 85.5:14.5 | 50.9 |
| 87 | CuCl₂ (1.34) | CaCO₃ (20) | n-propanol (100) | 78-80 | 35.9 | 85.2:14.8 | 20.5 |
| 88 | CuCl₂ (1.34) | MgCO₃ (16.88) | n-propanol (100) | 80-82 | 44.5 | 83.4:16.6 | 30.3 |
| 89 | CuCl₂ (1.34) | MgCO₃ (16.88) | n-butanol (100) | 73-84 | 60.5 | 83.6:16.4 | 48.2 |
| 90 | CuCl₂ (1.34) | CaCO₃ (20) | n-butanol (100) | 78-80 | 39.4 | 83:17 | 29.1 |

EXAMPLES 91-93

A mixture of ethylcyanoacetate, 1,1-dichloro-3,4-dibromo-4-methylpent-1-ene and calcium carbonate is

| Ex. | Copper salt and amount (parts) | Metal Chloride and amount (parts) | MgCO₃ or CaCO₃ and amount (parts) | Phase Transfer Catalyst | Reaction Time (hrs) | Reaction Temp. (°C.) | Strength (%) | cis-cyano trans-cyano ratio | Yield (%) |
|---|---|---|---|---|---|---|---|---|---|
| 94 | CuCl₂ (2.68) | CaCl₂ (44.0) | CaCO₃ (40) | MTEAC (1.8) | 14 | 74-78 | 71.1 | 64.1:35.9 | 69.7 |
| 95 | CuCl₂ (2.68) | MgCl₂ (38.08) | MgCO₃ (33.72) | CTMAB (1.8) | 14 | 76-80 | 59.2 | 67:33 | 55.1 |
| 96 | CuCl₂ (2.68) | CaCl₂ (59.4) | MgCO₃ (33.72) | CTMAB (1.8) | 14 | 80-85 | 66.9 | 69.3:30.6 | 64.7 |
| 97 | CuCl₂ (2.68) | CaCl₂ (44.0) | CaCO₃ (40) | MTEAC (6.06) | 14 | 82-86 | 75.7 | 67.6:32.4 | 73.1 |
| 98 | CuCl₂ (2.68) | CaCl₂ (44.0) | CaCO₃ (40) | CTMAB (1.8) | 14 | 73-74 | 73.6 | 68.3:31.7 | 68.0 |
| 99 | Cu₂Cl₂ (0.1) | CaCl₂ (60) | CaCO₃ (24) | MTEAC (6.06) | 14 | 78-80 | 25.4 | 60.6:39.4 | 28.8 |
| 100 | CuCl₂ (2.68) | CaCl₂ (60) | CaCO₃ (24) | MTEAC (6.06) | 14 | 80-82 | 60.8 | 65.8:34.2 | 60.3 |

-continued

| Ex. | Copper salt and amount (parts) | Metal Chloride and amount (parts) | MgCO₃ or CaCO₃ and amount (parts) | Phase Transfer Catalyst | Reaction Time (hrs) | Reaction Temp. (°C.) | Strength (%) | cis-cyano trans-cyano ratio | Yield (%) |
|---|---|---|---|---|---|---|---|---|---|
| 101 | CuCl₂ (0.26) | CaCl₂ (44) | CaCO₃ (40) | MTEAC (6.06) | 14 | 80–83 | 38.3 | 62.9:37.1 | 38.1 |
| 102 | CuCl₂ (2.68) | CaCl₂ (44) | CaCO₃ (40) | MTEAC (6.06) | 6 | 98–100 | 68.0 | 67.2:32.8 | 66.6 |
| 103 | CuCl₂ (2.68) | CaCl₂ (44) | CaCO₃ (40) | MTEAC (6.06) | 14 | 60–61 | 45.9 | 67.8:32.2 | 49.6 |
| 104 | CuCl₂ (2.68) | CaCl₂ (44) | CaCO₃ (40) | MTEAC (6.06) | 6 | 78–83 | 70.1 | 67.8:32.2 | 71.4 |
| 105 | CuCl₂ (2.68) | NaCl (46.8) | CaCO₃ (40) | MTEAC (6.06) | 6 | 82 | 58.5 | 66.8:33.2 | 58.8 |
| 106 | CuCl₂ (2.68) | Nil | CaCO₃ (40) | MTEAC (6.06) | 6 | 77–80 | 9.0 | 64.5:35.5 | 9.0 |

EXAMPLE 107

A mixture of malonitrile (14.52 parts), 1,1-dichloro-3,4-dibromo-4-methylpent-1-ene (62.2 parts), calcium carbonate (40 parts), cupric chloride (2.68 parts) and calcium chloride (44 parts) in ethanol (100 parts by volume) is heated to reflux and held at 78°–80° C. for 3.75 hours. The reaction mass is cooled and distilled under reduced pressure to remove ethanol and the residue is extracted with a mixture of toluene (100 parts by volume), water (150 parts) and hydrochloric acid (50 parts by volume). The resultant suspension is filtered and the residue is washed with toluene (2×50 parts by volume) and water (50 parts).

The residue is dried to give a brown solid (22.1 parts). The filtrates and washes are combined and separated and the toluene layer is washed with water (4×50 parts), then distilled under reduced pressure to yield crude product (17.3 parts) containing 1,1-dicyano-3-(2',2'-dichlorovinyl)-2,2-dimethylcyclopropane (14.04 parts). The brown solid (22.1 parts) is extracted at room temperature with toluene (100 parts by volume), then filtered and the residue washed with toluene. The filtrates are distilled under reduced pressure to yield a second crop of pure 1,1-dicyano-3-(2,2-dichlorovinyl)-2,2-dimethylcyclopropane (13.16 parts).

We claim:

1. A process for the preparation of a compound of formula:

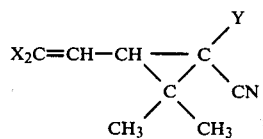

wherein both groups X are chlorine, bromine or trifluoromethyl, or one X is chlorine or bromine and the other is trifluoromethyl, and Y is —CN or —COOR in which R is an alkyl group of 1 to 4 carbon atoms, in which a compound of the formula:

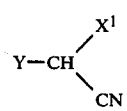

wherein X¹ is chlorine or bromine and Y has the meaning defined above, is reacted with a diene of the formula:

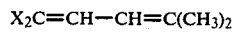

wherein X has the meaning defined above, the reaction taking place at a temperature from 0° to 140° C. for a time of 30 minutes to 30 hours, in the presence of from 0.01 to 0.1 mol per mol of the diene of a catalyst selected from the group consisting of metallic copper, cupric acetate, cupric chloride, copper stearate, cupric oxide, cuprous cyanide, cuprous chloride, copper acetylacetonate, di-μ-methoxobis(pentane-2,4-dionato)dicopper and di-μ-methoxobis(salicylaldehydato)dicopper, from 0.5 to 2.0 moles per mol of the diene of a base selected from the group consisting of an alkali or alkaline earth metal carbonate or borate, an alkali metal (1–4C) alkoxide and an alkaline earth metal oxide, and in a solvent selected from the group consisting of water together with a phase transfer catalyst, methanol, ethanol, isopropanol, tert.butanol, ethyl acetate, butyl acetate, acetonitrile, dimethylformamide, dimethylsulphoxide and N,N-dimethyl acetamide.

2. A process as claimed in claim 1 wherein the reaction is carried out in the presence of from 0 to 5 mols per mol of the diene of an alkali or alkaline earth metal salt or quaternary ammonium halide.

3. A process for the preparation of a compound of formula:

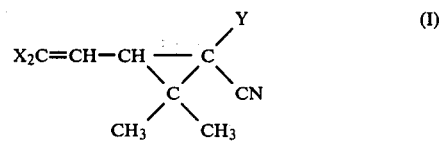

wherein both groups X are chlorine, bromine or trifluoromethyl, or one X is chlorine or bromine and the other is trifluoromethyl, and Y is —CN or —COOR in which R is an alkyl group of 1–4 carbon atoms, in which a compound of formula:

wherein Y has the meaning defined above, is reacted with a compound of the formula:

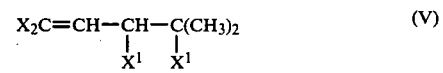

wherein X has the meaning defined above and X¹ is chlorine or bromine, the reaction taking place at a temperature from 0° to 140° C. for a time of from 30 minutes to 30 hours, in the presence of from 0.01 to 0.1 mol per mol of the compound of formula (V) of a catalyst selected from the group consisting of cupric chloride, cupric acetate, cuprous chloride, cuprous cyanide and basic cupric carbonate, and in a solvent selected from the group consisting of water together with a phase transfer catalyst, methanol, ethanol, isopropanol, tert-butanol, ethyl acetate, butyl acetate, acetonitrile, acetic acid, dimethylformamide, dimethylsulphoxide and N,N-dimethylacetamide.

4. A process as claimed in claim 3 wherein the reaction is carried out in the presence of from 1 to 2 moles per mol of the compound of formula (V) of a base selected from the group consisting of an alkali or alkaline earth metal carbonate, borate or acetate, an alkali metal (1-4C) alkoxide and an alkaline earth metal oxide.

5. A process as claimed in claim 3 wherein the reaction is carried out in the presence of from 0 to 4 mols per mol of the compound of formula (V) of a lithium, calcium, magnesium or quaternary ammonium halide.

6. A process as claimed in claim 3 wherein $X^1$ is bromine.

7. A process for the preparation of a compound of formula:

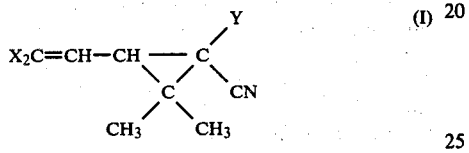
(I)

wherein both groups X are chlorine, bromine or trifluoromethyl, or one X is chlorine or bromine and the other is trifluoromethyl, and Y is —CN or —COOR in which R is an alkyl group of 1 to 4 carbon atoms, in which a compound of the formula:

(II)

wherein $X^1$ is chlorine or bromine and Y has the meaning defined above, is reacted with a diene of the formula:

$$X_2C=CH-CH=C(CH_3)_2 \qquad (III)$$

wherein X has the meaning defined above, the reaction taking place at a temperature of from 0° to 140° C. for a time of 30 minutes to 30 hours, in the presence of from 0.01 to 0.1 mol per mol of the diene of a catalyst selected from the group consisting of metallic copper, cupric acetate, cupric chloride, copper stearate, cupric oxide, cuprous cyanide, cuprous chloride, copper acetylacetonate, di-μ-methoxobis(pentane-2,4-dionato)dicopper and di-μ-methoxobis(salicylaldehydato)dicopper, from 0.5 to 2.0 mols per mol of the diene of a base selected from the group consisting of an alkali or alkaline earth metal carbonate or borate, an alkali metal (1-4C) alkoxide and an alkaline earth metal oxide, and in a solvent selected from the group consisting of water together with a phase transfer catalyst, methanol, ethanol, n-propanol, isopropanol, n-butanol, isobutanol, secondary butanol, tert.butanol, n-pentanol, isopentanol, n-hexanol, cyclohexanol, 2-methoxyethanol, 2-ethoxyethanol, methyl acetate, ethyl acetate, n-propyl acetate, isopropyl acetate, n-butyl acetate, isobutyl acetate, secondary butyl acetate, tert.butyl acetate, n-pentyl acetate, isopentyl acetate, n-hexyl acetate, cyclohexyl acetate, 2-methoxyethyl acetate, 2-ethoxyethyl acetate, acetonitrile, dimethylformamide, dimethylsulphoxide and N,N-dimethylacetamide.

8. A process for the preparation of a compound of formula:

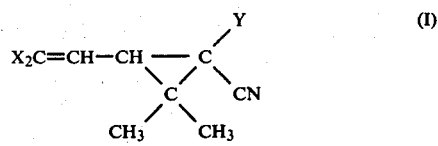
(I)

wherein both groups X are chlorine, bromine or trifluoromethyl, or one X is chlorine or bromine and the other is trifluoromethyl, and Y is —CN or —COOR in which R is an alkyl group of 1 to 4 carbon atoms, in which a compound of formula:

$$Y-CH_2-CN \qquad (IV)$$

wherein Y has the meaning defined above, is reacted with a compound of the formula:

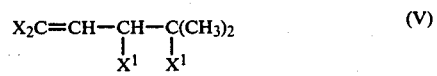
(V)

wherein X has the meaning defined above and $X^1$ is chlorine or bromine, the reaction taking place at a temperature from 0° to 140° C. for a time of from 30 minutes to 30 hours, in the presence of from 0.01 to 0.1 mol per mol of the compound of formula (V) of a catalyst selected from the group consisting of cupric chloride, cupric acetate, cuprous chloride, cuprous cyanide and basic cupric carbonate, and in a solvent selected from the group consisting of water together with a phase transfer catalyst, methanol, ethanol, n-propanol, isopropanol, n-butanol, isobutanol, secondary butanol, tert-.butanol, n-pentanol, isopentanol, n-hexanol, cyclohexanol, 2-methoxyethanol, 2-ethoxyethanol, methyl acetate, ethyl acetate, n-propyl acetate, isopropyl acetate, n-butyl acetate, isobutyl acetate, secondary butyl acetate, tert.butyl acetate, n-pentyl acetate, isopentyl acetate, n-hexyl acetate, cyclohexyl acetate, 2-methoxyethyl acetate, 2-ethoxyethyl acetate, acetonitrile, acetic acid, dimethylformamide, dimethylsulphoxide and N,N-dimethylacetamide.

* * * * *